United States Patent [19]

Bank

[11] Patent Number: 5,248,802
[45] Date of Patent: Sep. 28, 1993

[54] RUTHENIM CATALYZED PROCESS FOR PREPARATION OF β-CYANOALKYLSILANES

[75] Inventor: Howard M. Bank, Freeland, Mich.

[73] Assignee: Dow Corning Corporation, Midland, Mich.

[21] Appl. No.: 17,912

[22] Filed: Feb. 16, 1993

[51] Int. Cl.$^5$ ................................................ C07F 7/10
[52] U.S. Cl. ..................................................... 556/415
[58] Field of Search ........................................ 556/415

[56] References Cited

U.S. PATENT DOCUMENTS

| | | | |
|---|---|---|---|
| 2,860,453 | 11/1958 | Saam | 260/468.2 |
| 2,906,764 | 9/1959 | Jex et al. | 260/468.2 |
| 2,907,784 | 10/1959 | Jex et al. | 260/468.2 |
| 2,971,970 | 2/1961 | Bluestein | 260/468.2 |
| 5,126,467 | 6/1992 | Bank | 556/415 |
| 5,126,468 | 6/1992 | Bank | 556/415 |

OTHER PUBLICATIONS

Rajkumar et al., Organometallics 8:549 (1989).

*Primary Examiner*—Paul F. Shaver
*Attorney, Agent, or Firm*—William F. Boley

[57] ABSTRACT

The present invention is a process for the preparation of hydrolyzable β-cyanoalkylsilanes. More particularly, this invention relates to the catalytic addition of trichlorosilane to α,β-unsaturated olefinic nitriles to form β-cyanoalkylsilanes. The present process employs a catalyst comprising a ruthenium compound. The preferred catalyst for the present process is a ruthenium compound having at least one tertiary phosphine ligand. The process is conducted at a temperature within a range of about 50° C. to 300° C.

17 Claims, No Drawings

RUTHENIM CATALYZED PROCESS FOR PREPARATION OF β-CYANOALKYLSILANES

BACKGROUND OF INVENTION

The present invention is a process for the preparation of hydrolyzable β-cyanoalkylsilanes. More particularly, this invention relates to the catalytic addition of trichlorosilane to α,β-unsaturated olefinic nitriles to form β-cyanoalkylsilanes. The present process employs a catalyst comprising a ruthenium compound. The preferred catalyst for the present process is a ruthenium compound having at least one tertiary phosphine ligand.

Beta-cyanoalkylsilanes having hydrolyzable chlorines bonded to the silicon atom are useful for the production of polyorganosiloxanes containing the β-cyanoalkyl substituent. The silicon-bonded β-cyanoalkyl substituent is extremely resistant to hydrolysis and cleavage under hot, humid conditions and imparts these characteristics to the polyorganosiloxane of which they are a substituent. The presence of the silicon bonded β-cyanoalkyl substituent on polyorganosiloxanes also tends to stabilize the polyorganosiloxanes against swelling induced by liquid hydrocarbons. In addition, β-cyanoalkylsilanes having hydrolyzable chlorines are useful reactive intermediates for forming, for example, gamma-organoaminotrialkoxysilanes which are useful as surface treating agents.

It is known that when trichlorosilane is contacted with an olefinic nitrile, as exemplified by acrylonitrile, at a sufficient temperature a mixture of α-cyanoalkylsilanes and β-cyanoalkylsilanes is formed. In addition other reactions such as the formation of both silicon and non-silicon-containing complexes, homopolymerization of the starting nitrile, and the disproportionation of the starting silane can occur. The α-cyanoalkylsilanes are hydrolytically unstable. Therefore, the β-cyanoalkylsilanes generally have more commercial utility than the α-cyanoalkylsilanes and processes for producing high yields of β-cyanoalkysilanes are desirable.

A number of catalyst have been reported useful in the preparation of β-cyanoalkylsilanes. Saam, U.S. Pat. No. 2,860,153, issued Nov. 11. 1958. describe a process for preparing β-cyanoethyltrichlorosilane by heating at a temperature less than 150° C. a mixture of acrylonitrile and trichlorosilane with a catalytic amount of an amine.

Jex et al., U.S. Pat. No. 2,906,764, issued Sep. 29, 1959, describe a process where organosilanes having at least one hydrogen and one hydrolyzable group bonded to silicon are reacted with an alkene nitrile in the presence of a diarylamine catalyst to produce preferentially β-cyanoalkylsilanes.

Jex et al., U.S. Pat. No. 2.907.784, issued Oct. 6, 1959, describe a process where organosilanes having at least one hydrogen and one hydrolyzable group bonded to silicon are reacted with an alkene nitrile in the presence of a trihydrocarbylphosphine catalyst to produce preferentially β-cyanoalkylsilanes.

Bluestein, U.S. Pat. No. 2.971.970, issued Feb. 14, 1961, describes a multiple component catalyst system useful for the production of β-cyanoalkylsilanes by the reaction of alkene nitriles with organosilanes having at least one hydrogen. The catalyst comprises a cuprous compound, a diamine, and a trialkylamine.

Rajkumar et al., Organometallics 8:549 (1989), describe a two-component catalyst effective in hydrosilation of acrylonitrile leading to the β-addition to the double bond of the acrylonitrile. The catalysts consist of cuprous oxide and tetramethylethylenediamine.

Bank, U.S. Pat. No. 5,126.468, issued Jun. 30, 1992, describes a process for the preparation of hydrolyzable β-cyanoalkylsilanes. The process employs novel catalysts comprising a diamine and non-activated copper, selected inorganic copper compounds, and di-coordinate organic copper compounds.

Bank, U.S. Pat. No. 5,126,469, issued Jun. 30, 1992, describes a process for the preparation of hydrolyzable β-cyanoalkylsilanes. The process employs a catalyst comprising a diamine and supported copper or a supported copper compound.

SUMMARY OF INVENTION

The present invention is a process for the preparation of hydrolyzable β-cyanoalkylsilanes. More particularly, this invention relates to the catalytic addition of trichlorosilane to α,β-unsaturated olefinic nitriles to form β-cyanoalkylsilanes. The present process employs a catalyst comprising a ruthenium compound. The preferred catalyst for the present process is a ruthenium compound having at least one tertiary phosphine ligand. The process is conducted at a temperature within a range of about 50° C. to 300° C.

DESCRIPTION OF INVENTION

The present invention is a process for preparation of β-cyanoalkylsilanes described by formula

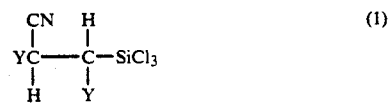  (1)

The process comprises: contacting a mixture comprising trichlorosilane and an olefinic nitrile described by formula

  (2)

with an effective concentration of a ruthenium compound catalyst at a temperature within a range of about 50° C. to 200° C.; where each Y is independently selected from a group consisting of hydrogen and alkyl radicals comprising one to eight carbon atoms.

In carrying out the process of the present invention, the olefinic nitrile, the trichlorosilane, and the ruthenium compound catalyst are contacted in a suitable reactor. The type of reactor is not critical to the present process. However, those skilled in the art will recognize that certain metals and metal complexes such as nickel chloride amine complexes can catalyze the formation of the α-adducts of the olefinic nitriles. Therefore, it is desirable to perform the process in reactors formed from non-reactive materials.

The present process can be run as a batch, semi-batch, or continuous process. The reactor can be, for example, a continuous-stir-tank reactor. When the ruthenium compound catalyst is a heterogeneous catalyst, the reactor can be, for example, a packed-bed, a stirred-bed, a vibrating-bed, or a fluidized-bed type reactor. Preferred is when the process is run as a batch or continuous process.

A mixture comprising trichlorosilane and an olefinic nitrile as described by formula (2) is contacted with a ruthenium compound catalyst. The mixture may be formed by feeding the trichlorosilane and olefinic nitrile separately to an appropriate reactor, or alternatively the mixture may be preformed and then fed to the reactor.

Contact of the mixture comprising trichlorosilane and an olefinic nitrile with the ruthenium compound catalyst can be effected by feeding the mixture to a reactor containing the ruthenium compound catalyst. When the ruthenium compound catalyst is a homogeneous catalyst, the ruthenium compound catalyst can be premixed with one or more of the components forming the mixture comprising the trichlorosilane and an olefinic nitrile and this mixture then fed to the heated reactor. The homogeneous ruthenium compound catalyst and the mixture comprising trichlorosilane and an olefinic nitrile can be fed separately to the reactor.

Olefinic nitriles useful in the present invention are described by formula (2), where each Y is independently selected from a group consisting of hydrogen and alkyl radicals comprising one to eight carbon atoms. The substituent Y can be, for example, hydrogen, methyl, ethyl, propyl, butyl, tert-butyl, and octyl. Preferred is when each substituent Y is independently selected from a group consisting of hydrogen and methyl. The olefinic nitrile can be, for example, acrylonitrile, methacrylonitrile, crotononitrile, ethylacrylonitrile, 1-cyanobutene-1, and 2-cyanooctene-1. Preferred is when the olefinic nitrile is acrylonitrile.

The trichlorosilane is provide to the reactor at a molar ratio within a range of about 0.9:1 to 100:1 in relation to the olefinic nitrile. Lessor molar ratios of trichlorosilane may be used but can result in reduced yields of the desired $\beta$-cyanoalkylsilane. Greater molar ratios of trichlorosilane may be used in the process, but may result in reduced process yields due to dilution of the olefinic nitrile. It is preferred that the molar ratio of trichlorosilane to olefinic nitrile be within a range of about 1:1 to 50:1.

The mixture comprising the trichlorosilane and an olefinic nitrile is contacted with a ruthenium compound catalyst. By "ruthenium compound catalyst" it is meant those compounds of ruthenium which catalyze the beta-silation of an olefinic nitrile as described by equation (2) with trichlorosilane. Preferred is when the ruthenium compound catalyst is selected from a group consisting of ruthenium halides and ruthenium compounds having at least one tertiary phosphine ligand. Examples of ruthenium halide compounds which may be useful as catalysts in the present process include $RuCl_3$, $RuCl_3 \cdot H_2O$, $RuI_3$, and hydrated $RuBr_3$. The preferred ruthenium halide compound is $RuCl_3$. Examples of ruthenium compounds having at least one tertiary phosphine ligand, which may be useful as catalysts in the present process, include $Ru(CO)_3(PPh_3)_2$, $RuCl_2(CO)_2(PPh_3)_2$, $RuCl_2(PPh_3)_4$, $RuH_2(PPh_3)_4$, $Ru(CH_2=CH_2)(PPh_3)_3$, $RuHCl(PPh_3)_3 \cdot C_7H_6$ complex, and $RuHCl(PPh_3)_3$. The preferred ruthenium compound having at least one tertiary phosphine ligand is tris(triphenylphosphine)ruthenium(II) chloride i.e. $RuCl_2(PPh_3)_3$.

In the present process, an effective concentration of a ruthenium compound catalyst is that which increases the rate of formation of the $\beta$-cyanoalkylsilane, improves the yield of $\beta$-cyanoalkylsilane, or both, in relation to the uncatalyzed process. A preferred effective concentration of the ruthenium compound catalyst is that which provides to the process a ruthenium concentration within a range of about 0.001 to 10 mole percent. A more preferred effective concentration of the ruthenium compound catalyst is that which provides to the process a ruthenium concentration within range of about 0.05 to 1.0 mole percent.

The process is conducted at a temperature within a range of about 50° C. to 300° C. The preferred temperature for conducting the present process is within a range of about 100° C. to 170° C.

The present process is applicable for the preparation of $\beta$-cyanoalkylsilanes as exemplified by $\beta$-cyanoethyltrichlorosilane, $\beta$-cyano($\alpha$-methyl)ethyltrichlorosilane, $\beta$-cyano($\beta$-methyl)ethyltrichlorosilane, $\beta$-cyano($\alpha$-ethyl)ethyltrichlorosilane, and $\beta$-cyano($\beta$-ethyl)ethyltrichlorosilane.

The following examples are provided to illustrate the present invention. The examples are not intended to limit the scope of the present claims.

Example 1. The ability of tris(triphenylphosphine)ruthenium(II) chloride to catalyzed the reaction of trichlorosilane with acrylonitrile to form a $\beta$-cyanoalkylsilane was evaluated. The process was conducted in a sealed 8 mm×35 cm glass tube, heat dried, and purged with argon. About 0.011 g of $RuCl_2(PPh_3)_3$ was added to the tube. Then, approximately 2.0 mL of a mixture comprising the acrylonitrile (AN) and 5.0 mole percent excess trichlorosilane was added to the tube. The tube was heated at 120° C. for two hours. The content of the tube was cooled and then analyzed by gas liquid chromotography (GLC) using a thermal conductivity (TC) detector. The results are presented in Table 1 as percent area under the readout curve (GLC-TC Area %) for each of the described compounds.

TABLE 1

| | Reaction of Trichlorosilane With Acrylonitrile Using $RuCl_2 (PPh_3)_3$ as Catalyst. | | | | | |
|---|---|---|---|---|---|---|
| $H_2SiCl_2$ | $HSiCl_3$ | AN | $SiCl_4$ | $Cl_2HSi(CH_2)_2CN$ | $Cl_3Si(CH_2)_2CN$ | Unknown |
| 0.0 | 7.0 | 12.1 | 13.8 | 0.9 | 60.6 | 2.5 |

Example 2. The ability of ruthenium trichloride to catalyze the reaction of trichlorosilane with acrylonitrile to form a $\beta$-cyanoalkylsilane was evaluated. The process was conducted in a sealed glass tube as described for example 1. About 0.0175 g of $RuCl_3$ was added to the tube. Then, approximately 2.0 mL of a mixture comprising acrylonitrile (AN) and trichlorosilane at about molar equivalence was added to the tube. The tube was heated at 120° C. for two hours. After heating the amber solution contained black solids suggesting the catalyst did not completely dissolve. The content of the tube was cooled and the amber liquid analyzed by GLC-TC. The results are presented in Table 1 as percent area under the readout curve (GLC-TC Area %) for each of the described compounds.

TABLE 2

| | Reaction of Trichlorosilane With Acrylonitrile Using $RuCl_3$ as Catalyst | | | | |
|---|---|---|---|---|---|
| $H_2SiCl_2$ | $HSiCl_3$ | AN | $SiCl_4$ | $Cl_3Si(CH_2)_2CN$ | Unknown |
| 0.5 | 24.5 | 57.9 | 10.0 | 5.1 | 0.2 |

I claim:

1. A process for preparation of β-cyanoalkylsilanes described by formula

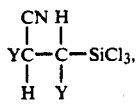

the process comprising: contacting a mixture comprising trichlorosilane and an olefinic nitrile described by formula

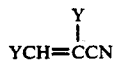

with an effective concentration of a ruthenium compound catalyst at a temperature within a range of about 50° C. to 300° C.; where each Y is independently selected from a group consisting of hydrogen and alkyl radicals comprising one to eight carbon atoms.

2. A process according to claim 1, where each substituent Y is independently selected from a group consisting of hydrogen and methyl.

3. A process according to claim 1, where the olefinic nitrile is selected from a group consisting of acrylonitrile, methacrylonitrile. crotononitrile, ethylacrylonitrile, 1-cyanobutene-1, and 2-cyanooctene-1.

4. A process according to claim 1, where the olefinic nitrile is acrylonitrile.

5. A process according to claim 1, where the trichlorosilane is provided to the reactor at a molar ratio within a range of about 0.9:1 to 100:1 in relation to the olefinic nitrile.

6. A process according to claim 1, where the trichlorosilane is provided to the reactor at a molar ratio within a range of about 1:1 to 50:1 in relation to the olefinic nitrile.

7. A process according to claim 1, where the ruthenium compound catalyst is selected from a group consisting of ruthenium halides and ruthenium compounds having at least one tertiary phosphine ligand.

8. A process according to claim 1, where the ruthenium compound catalyst is a ruthenium halide selected from a group consisting of $RuCl_3$, $RuCl_3.H_2O$, $RuI_3$, and hydrated $RuBr_3$.

9. A process according to claim 1, where the ruthenium compound catalyst is $RuCl_3$.

10. A process according to claim 1, where the ruthenium compound catalyst is a ruthenium compound having at least one tertiary phosphine ligand and is selected from a group consisting of $Ru(CO)_3(PPh_3)_2$, $RuCl_2(CO)_2(PPh_3)_2$, $RuCl_2(PPh_3)_4$, $RuH_2(PPh_3)_4$, $Ru(CH_2\!\!=\!\!CH_2)(PPh_3)_3$, $RuHCl(PPh_3)_3.C_7H_8$ complex, and $RuHCl(PPh_3)_3$.

11. A process according to claim 1, where the ruthenium compound catalyst is $RuCl_2(PPh_3)_3$.

12. A process according to claim 1, where concentration of the ruthenium compound catalyst provides to the process a ruthenium concentration within a range of about 0.001 to 10 mole percent.

13. A process according to claim 1, where concentration of the ruthenium compound catalyst provides to the process a ruthenium concentration within a range of about 0.05 to 1.0 mole percent.

14. A process according to claim 1, where the process is conducted at a temperature within a range of about 100° C. to 170° C.

15. A process according to claim 1, where the β-cyanoalkylsilane is selected from a group consisting of β-cyanoalkylsilanes as exemplified by β-cyanoethyltrichlorosilane, β-cyano(α-methyl)ethyltrichlorosilane, β-cyano(β-methyl)ethyltrichlorosilane, β-cyano(α-ethyl)ethyltrichlorosilane, and β-cyano(β-ethyl)ethyltrichlorosilane.

16. A process according to claim 1,. where the olefinic nitrile is selected from a group consisting of acrylonitrile. methacrylonitrile, crotononitrile. ethylacrylonitrile, 1-cyanobutene-1, and 2-cyanooctene-1; the trichlorosilane is provided to the reactor at a molar ratio within a range of about 1:1 to 50:1 in relation to the olefinic nitrile; the ruthenium compound catalyst is $RuCl_2(PPh_3)_3$; ruthenium concentration in the process is within a range of about 0.05 to 1.0 mole percent; and the temperature is within a range of about 100° C. to 170° C.

17. A process according to claim 1, where the olefinic nitrile is acrylonitrile.

* * * * *